United States Patent [19]

Hogan

[11] Patent Number: 5,137,515
[45] Date of Patent: Aug. 11, 1992

[54] SAFETY DEVICE FOR REMOVAL AND DISPOSAL OF MEDICAL NEEDLES

[75] Inventor: J. Martin Hogan, Long Beach, Calif.

[73] Assignee: City of Hope, Duarte, Calif.

[21] Appl. No.: 115,403

[22] Filed: Nov. 2, 1987

[51] Int. Cl.⁵ ............................................. A61M 5/00
[52] U.S. Cl. .................................. 604/110; 604/164; 604/263
[58] Field of Search ........................ 604/158-170, 604/192, 198, 263; 128/763-765; 206/364, 365

[56] References Cited

U.S. PATENT DOCUMENTS

| | | | |
|---|---|---|---|
| 3,438,373 | 4/1969 | Pannier | 604/159 |
| 3,592,192 | 7/1971 | Harautuneian | 604/165 |
| 4,139,009 | 2/1979 | Alvarez | 604/198 |
| 4,160,450 | 7/1979 | Doherty | 604/164 |
| 4,177,809 | 12/1979 | Moorehead | 604/164 |
| 4,643,199 | 2/1987 | Jennings, Jr. et al. | 128/763 |
| 4,650,468 | 3/1987 | Jennings, Jr. | 604/110 |
| 4,676,783 | 6/1987 | Jagger et al. | 604/198 X |
| 4,725,267 | 2/1988 | Vaillancourt | 604/192 |
| 4,728,322 | 3/1988 | Walker et al. | 604/165 |
| 4,735,618 | 4/1988 | Hagen | 604/198 X |
| 4,747,831 | 5/1988 | Kulli | 604/198 X |
| 4,762,516 | 8/1988 | Luther et al. | 604/164 |

OTHER PUBLICATIONS

Webster's Dictionary, 9th Ed., 1984, p. 202.

*Primary Examiner*—John D. Yasko
*Assistant Examiner*—Anthony Gutowski
*Attorney, Agent, or Firm*—Edward S. Irons

[57] ABSTRACT

A sheath and method for the removal and disposal of removable needles used to guide insertion of catheters. The sheath having a one way entrance for allowing the removable needle to be taken into the sheath by pulling on a wire attached to the removable needle and passed through the sheath, but to prevent the removable needle from coming out of the sheath after the removable needle is in the sheath.

7 Claims, 2 Drawing Sheets

SAFETY DEVICE FOR REMOVAL AND DISPOSAL OF MEDICAL NEEDLES

FIELD OF INVENTION

This invention relates to a protective sheath apparatus and method for safely removing needles inserted in patients which have been used to guide catheters into the patients for withdrawing or injecting fluids in such a way as to protect medical personnel from being punctured by the removed needles. Additionally, the apparatus of the present invention completely encases the entire length of a removed needle even when the needle is thrown away, thus protecting all persons who handle the apparatus with the encased needle.

BACKGROUND OF THE INVENTION

Catheters with removable needle inserts for guiding the catheters into patients are known. An example of such catheters is described in U.S. Pat. No. 4,177,809, issued Dec. 11, 1979. The catheter and removable needle described there includes a wire attached to the needle which can be used to pull the removable needle out of the catheter after the catheter is inserted into a patient. A danger to medical personnel using such catheters with removable needles is the possibility that after a needle has punctured a patient and been contaminated by contact with tissue and fluids, harmful material could be injected into persons handling the needle by unintentionally breaking their skin with the contaminated needle point. The spread of hepatitis to medical personnel treating patients by inadvertent pricking of their skin with contaminated needles is a known hazard that continues to occur. Another fatal disease which can be transmitted by contaminated needles is Acquired Immune Deficiency Syndrome (AIDS).

The present invention avoids the spreading of diseases through inadvertent skin pricking by contaminated removable needles from catheters by providing a means and method for withdrawing removable needles directly into a totally encasing sheath. The contaminated removable needles can then be safely handled and disposed.

SUMMARY OF THE INVENTION

The type of catheter apparatus of interest here are catheters enclosing needles which are withdrawn by pulling on wires attached to the needles after the catheters are inserted into a patient's vein or artery. Such catheters are sold under the trademark "Angio-Set" by Deseret Medical, Inc., Sandy, Utah 84070. Their construction and operation are disclosed in previously cited U.S. Pat. No. 4,177,809.

The removable needle is used to guide an enclosing catheter into either a patient's vein or artery. After guiding the catheter into a vein or artery, the needle is removed leaving the catheter, which can be made of more pliable material than the needle, inserted in the patient. When such a catheter with a removable needle is inserted into a patient a tube is also attached to the catheter through which the wire attached to the removable needle can be pulled so that the needle can be withdrawn from the catheter and through the tube. The present invention provides a sheath attached at the opposite end of the tube from the catheter. The wire attached to the removable needle runs through both the tube and the sheath of the present invention. By pulling the wire the needle is drawn out of the catheter through the tube and into the sheath of the present invention. The sheath is longer than the body of the removable needle, and the removable needle is retained in the sheath so that the entire length of the removable needle is encased. At the end of the sheath opposite the catheter there is an opening large enough to allow the wire attached to the needle to pass through but too small to allow the removable needle to pass through. At the front end of the sheath where the removable needle enters the sheath there is a structure provided which allows the needle to be easily drawn into the sheath but does not permit the needle to pass back out of the sheath. Other embodiments of the sheath include curved interior surfaces which inhibits movement of an encased needle and thus further assures that once inside a sheath of the present invention a needle will not come out. Another embodiment of the present invention includes a structure at the back end of the sheath with a tapered opening through which the wire can be drawn but in which the needle becomes wedged because the tapered opening narrows to a diameter smaller than that of the needle. The wire is pulled until the needle is wedged in the opening and the sheath extends well beyond the pointed tip of the needle.

BRIEF DESCRIPTION OF THE DRAWINGS

The novel features of the invention will be more readily associated with the following description when read in conjunction with the appended drawings, in which corresponding components are designated by the same reference numerals throughout the various figures.

DETAILED DESCRIPTION OF THE INVENTION

Figure 1:
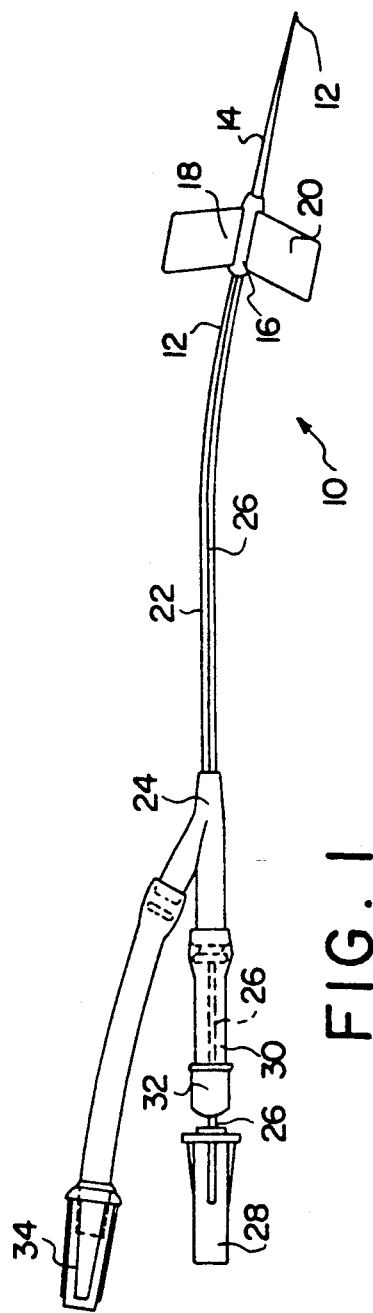
FIG. 1 is a perspective drawing of a known catheter with a removable needle and its attached wire.

Shown in FIG. 1 is a previously known catheter apparatus 10. The catheter apparatus 10 includes a removable hollow needle 12, a catheter tube 14, inserter 16, with insertion wings 18 and 20, a trailing tube 22, and a Y-adaptor 24. Attached, such as by welding, brazing, crimping, gluing or other method assuring strong attachment, to the proximal end of the removable needle 12 is a flexible filament or wire 26. At the opposite end of the wire 26 from the removable needle 12 is a handle 28 for pulling the wire 26 to remove the needle 12 from the catheter apparatus 10. One of the branches from the Y-adapter 24 includes an extension tube 30 with a self-sealing plug 32 attached at the end of the extension tube 30. The wire 26, which is attached to the removable needle 12, passes through the self-sealing plug 32. Attached to the other branch of the Y-adaptor 24 is a closure cap 34. Construction and operation of the catheter apparatus 10 shown in FIG. 1 and of alternative embodiments are set out in previously cited U.S. Pat. No. 4,177,809.

Figure 2:
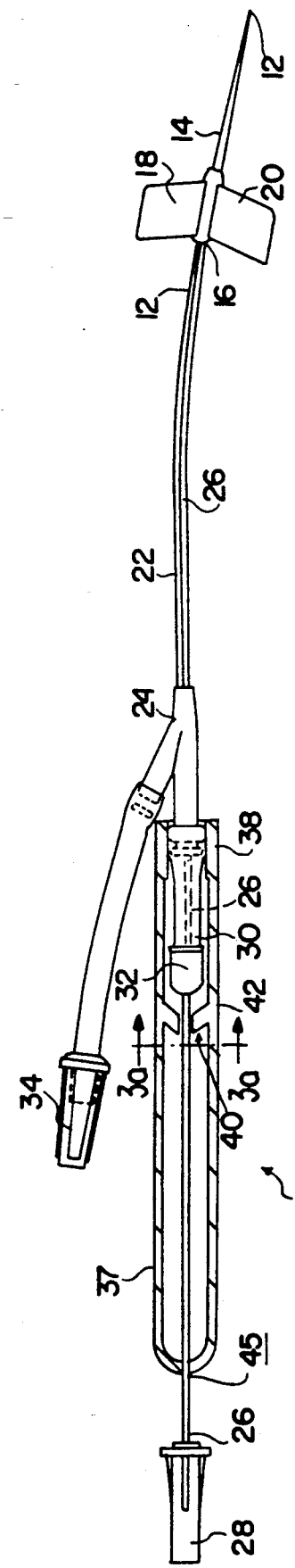
FIG. 2 is a perspective drawing of the catheter of FIG. 1 with a sheath of the present invention attached to the catheter apparatus.
Figure 3:
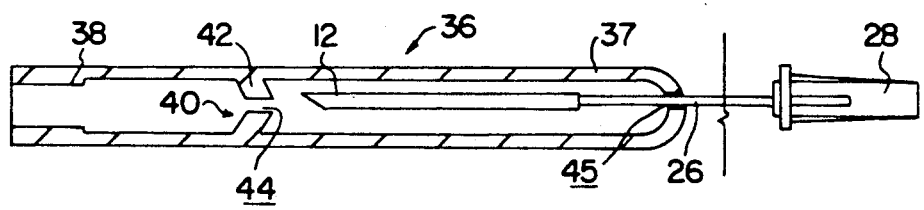
FIG. 3 is a sectional side view of the sheath shown in FIG. 2 with a removable needle encased in the sheath.
Figure 3A:
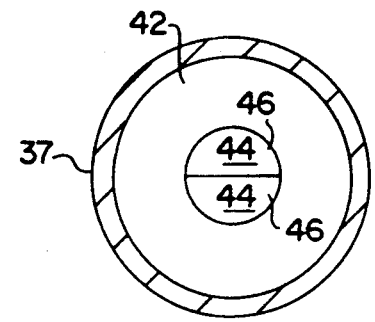
FIG. 3a is another sectional drawing of the sheath shown in FIG. 2 showing the one way entrance system for allowing a removable needle to be drawn into a sheath but preventing the removable needle from coming out of the sheath.

A protective sheath according to a preferred embodiment of the present invention is shown in FIG. 2 where it is generally designated by reference numeral 36. The body 37 of the protective sheath 36 can be made of injection molded plastic or other material such as extruded sheet metal. The chief requirement for the material is that it be durable and be capable of withstanding rough treatment such as being dropped or stepped on without breaking. Attachment of the protective sheath 36 to the catheter apparatus 10 can be by a friction fit. The end of the protective sheath 36 through which the removable needle 12 is passed into the protective sheath 36 can have a beveled opening 38. The beveled opening 38 has its widest opening for accepting the extension tube 30 at the open end of the sheath 36 and narrows down on the extension tube 30 toward the interior of the sheath 36. The beveled opening 38 when fitted over the extension tube 30 provides a fiction fit at the joint between the extension tube 30 and the Y-adaptor 24. Other systems of joining the sheath 36 to the catheter apparatus 10 can be used such as known threaded joints, spot welds which can be easily broken or bayonet joints. The requirements for the joint between the catheter apparatus 10 and the sheath 36 is that prior to withdrawing the removable needle 12 from the catheter the sheath 36 be securely attached to the catheter apparatus 10 so that the two do not separate while being manipulated by medical personnel. After the removable needle 12 has been drawn into the sheath 36 then the joint between the sheath 36 and the catheter apparatus 10 must be able to be disassembled easily. All of the joint systems listed above, i.e., friction, threaded, spot welds which can be easily broken and bayonet, are known to meet these requirements.

A one way entrance 40 system is positioned in the sheath 36 toward the open end through which the removable needle 12 enters. The one way entrance 40 allows the removable needle 12 to be drawn into the sheath 36 but prevents the removable needle 12 from coming out of the sheath 12 once inside. To accomplish its function, the one way entrance 40 can be made in the slope of a disc 42 positioned in the sheath 36 with a hole 44 in the center of the disc 42 through which the removable needle 12 can pass. The surface of the disc 42 on the inside of the sheath 36 can be shaped so that when a removable needle 12 has passed through the one way entrance 40 and is inside the sheath 36 the hole 44 in the disc 42 is at the apex of the remainder of the disc 42 surface. So when the point of the removable needle 12 moves toward the one way entrance 40, the surface of the disc 42 will tend to move the point of the removable needle 12 away from the hole 44. Further enhancing the capability of the one way entrance 40 to retain a removable needle 12 in a sheath 36 is the design of the hole 44 in the disc 42. One design is to select the diameter of the hole 44 so there is a friction fit between the removable needle 12 and the disc 42. The friction fit will allow the wire 26 to pull the removable needle 12 through the hole 44 but will prevent the removable needle 12 from falling back out through the hole 44 or being pushed through the hole 44 because the wire 26 is not stiff enough to provide the necessary force to push the needle 12 through the hole 44. Another acceptable design is to insert deformable lips 46 in the hole 44. The deformable lips 46 can be made of flexible plastic which permit the removable needle 12 to be pulled through the hole 44 but which close after the removable needle 12 has passed through the hole 44. Thus preventing the removable needle 12 from coming out of the sheath 36.

At the end of the sheath 36 furthest from the open end where the removable needle 12 can be drawn into the sheath 36 there is a hole 45 placed in the body 37 of the sheath 36. The wire 26 which is attached to the removable needle 12 is passed through the hole 45. The diameter of the hole 45 is large enough to pass the wire 26 but too small to pass the removable needle 12. The removable needle 12 may be further or alternatively restrained from passing through the hole 45 by use of a washer or bead (not shown) made of plastic or metal with a central hole large enough for the wire 26 to pass through but too small to allow the removable needle 12 to pass through. So with a bead or washer on the wire 26 between the hole 45 in the sheath 36 and the removable needle 12 the removable needle 12 will not pass out of the sheath 36 through the hole 45. Thus, with the sheath 36 joined to the catheter apparatus 10, and the wire 26 passed through the one way entrance 40 and the hole 45 in the body 37, the wire 26 can be pulled to draw the removable needle 12 into the sheath 36. Then the sheath 36 can be removed from the catheter apparatus 10 and safely disposed of with the removable needle 12 encased in the sheath 36.

Figure 4:
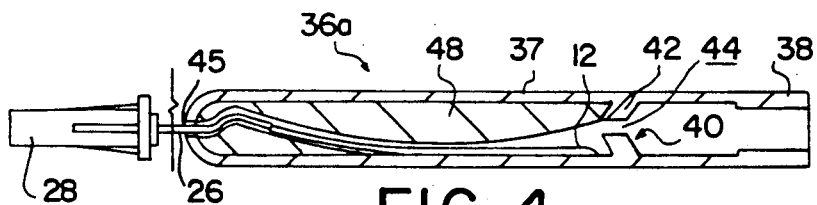
FIG. 4 is a sectional side view of a sheath which can be attached to the catheter apparatus as shown in FIG. 2 with an alternative interior design for retaining a removable needle.
Figure 5:
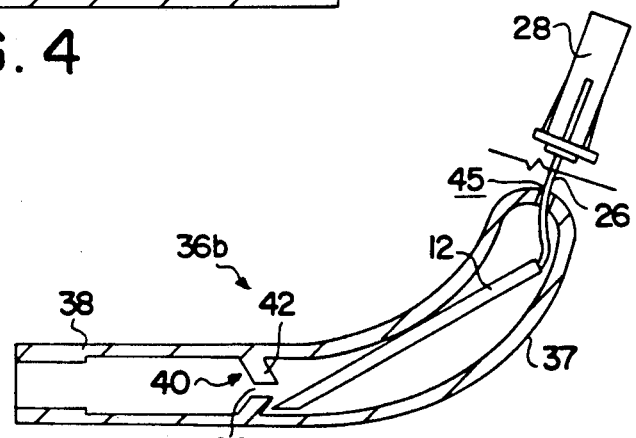
FIG. 5 is a sectional side view of a sheath which can be attached to the catheter apparatus as shown in FIG. 2 with an alternative interior design for retaining a removable needle.
Figure 6:
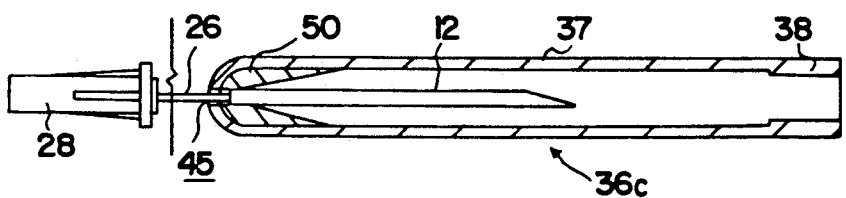
FIG. 6 is a sectional side view of a sheath which can be attached to the catheter apparatus as shown in FIG. 2 with an alternative interior design for retaining a removable needle.

Shown in FIGS. 4, 5 and 6 are alternative embodiments for the sheath 36. All of the sheaths shown in FIGS. 4, 5 and 6 are made of material which will withstand impacts comparable to being dropped or compression forces comparable to being stepped on without breaking.

The sheath shown in FIG. 4 and generally designated 36a includes a one way entrance 40 system consisting of a disc 42 and a hole 44. But in this case, the hole 44 does not necessarily have to be sized to provide a friction fit with the removable needle 12 or include deformable lips 46. Here an encasement system 48 is provided inside the sheath 36a to firmly retain the removable needle after it is drawn into the sheath 36a. The encasement system 48 can be made of molded plastic with a curved channel for receiving the removable needle 12. The curved channel permits entrance of the removable needle 12 into the sheath 36a through the one way entrance 40 but then flexes the removable needle 12 as the removable needle 12 is drawn into the sheath 36a. When drawn into the sheath 36a so that the point of the removable needle 12 has passed through the one way entrance 40, the removable needle 12 is flexed with the point retained adjacent to the sheath 36a body 37 and the end where the wire 26 is attached to the removable needle 12 is flexed toward the opposite side of the body 37. To prevent the removable needle 12 from being drawn completely through the sheath 36a a hole can be placed at the end of the sheath 36a which is smaller than the diameter of the removable needle 12 but larger than the wire 26 used to pull the removable needle 12. Alternatively, the channel in the encasement system 48 at the end of the sheath 36a opposite the one way entrance 40 can be curved more sharply than the removable needle 12 can be bent by pulling on the wire 24. Thus the removable needle 12 cannot be pulled past this sharper curve in the encasement system 48.

The sheath shown in FIG. 5 and generally designated 36b has a bent body 37 for retaining removable needles 12. The sheath 36b includes a one way entrance 40 system consisting of a disc 42 and a hole 44. Again the hole 44 does not necessarily have to be sized to provide a friction fit with the removable needle 12 or include deformable lips 46. The bend in the body 37 is sharp enough that when the removable needle 12 is drawn into the sheath 36b the point of the removable needle 12 cannot be moved back to the hole 44 in the one way entrance 40 without flexing the removable needle 12 such that the end of the removable needle 12 where the wire 26 is attached to the removable needle 12 is in contact with the body 37 and the middle portion of the removable needle 12 is also in contact with the body 37. As encased in the sheath 36b, no set of forces can be applied to the removable needle 12 to accomplish this distortion of the removable needle 12 by the only mechanical connection to the removable needle 12, namely the wire 26 which is not stiff enough to push and so bend the removable needle 12. Further, the disc 42 of the one way entrance 40 is beveled into the sheath 36b, so as the removable needle 12 is pushed toward the entrance of the sheath 36b, the point is lodged in a concentric hole formed by the disc 42 and the body 37.

The sheath shown in FIG. 6 and generally designated 36c includes a wedged holder 50 at the base end. Here it is not required that a one way entrance 40 be used. Instead the length of the body 37 is longer than the length of the removable needle 12. At the end of the sheath 36c opposite the end where the removable needle 12 is drawn into the sheath 36c a wedged holder 50 is positioned. The wedged holder 50 can be made of molded plastic. The wedged holder 50 includes a central passage through which the wire 26 attached to the removable needle 12 can pass. This central passage has a decreasing diameter from the end where the wire 26 can be used to pull the removable needle 12 into the sheath 36c. At the widest portion of the passage the full diameter of the removable needle 12 can pass. However, as the removable needle 12 is drawn further into the wedged holder the diameter of the passage in the wedged holder 50 becomes smaller than the diameter of the removable needle 12. So pulling the removable needle 12 into the wedged holder 50 causes the removable needle 12 to be held firmly in the wedged holder 50. Since the force which can be applied to the removable needle 12 by pulling on the wire 26 is much greater than any force which can be applied to the removable needle 12 by pushing on the wire 26, the removable needle 12 will be permanently retained in the wedged holder 50.

The features of the embodiments shown in FIGS. 3-6 can be used in various combinations as long as the selected combination results in a sheath which can be used to continuously encase a removable needle 12 from the time it is removed from a patient.

The above discussion and related illustrations of the present invention are directed primarily to preferred embodiments and practices of the invention. However, it is believed that numerous changes and modifications in the actual implementation of the concepts described herein will be apparent to those skilled in the act, and it is contemplated that such changes and modifications may be made without departing from the scope of the invention as defined by the following claims.

What is claimed is:

1. In a catheter assembly having a cannula having a proximal end portion, a distal end portion and a longitudinal duct therethrough from said proximal end portion to said distal end portion; a longitudinal piercing member having a proximal end and distal end having a sharp insertion tip, the longitudinal piercing member being positioned within the longitudinal duct of the cannula with the insertion tip extending beyond the distal end of the cannula; a hub having a passageway therethrough from the proximal end to the distal end thereof, the proximal end portion of the cannula being attached adjacent the distal end of the hub with the passageway in flow communication with the duct in the proximal end portion of the cannula; and an extraction wire having proximal and distal ends, said wire being of smaller diameter than the longitudinal piercing member, having said distal end thereof attached to extend longitudinally from the proximal end of the longitudinal piercing member, said extraction wire extending through the duct of the cannula and through the passageway of the hub to said proximal end of said wire, an improvement comprising:

a rigid longitudinal piercing member receiving tube having proximal and distal end portions and a longitudinal bore therethrough from said proximal to said distal end portion, said tube being adjacent to said proximal end of said hub, said extractor wire extending from said passageway through and beyond said bore of said tube;

a first closure across said proximal end portion of said tube, said first closure having a generally central opening large enough to allow said wire to pass longitudinally therethrough but too small to allow said longitudinally piercing member to pass fully longitudinally therethrough;

a second closure across said distal end portion of said tube, said second closure having a generally central access through which said wire and said longitudinal piercing member can longitudinally pass; and wherein said second closure includes means for automatically entrapping said insertion tip of said longitudinal piercing member in said longitudinal bore of said receiving tube, said entrapping means operating in response to said longitudinal piercing member being moved fully proximally into said receiving tube by proximal movement of said extraction wire.

2. In a catheter assembly having a cannula having a proximal end portion, a distal end portion and a longitudinal duct therethrough from said proximal end portion to said distal end portion; a longitudinal piercing member having a proximal end and distal end having a sharp insertion tip, the longitudinal piercing member being positioned within the longitudinal duct of the cannula with the insertion tip extending beyond the distal end of the cannula; a hub having a passageway therethrough from the proximal end to the distal end thereof, the proximal end portion of the cannula being attached adjacent the distal end of the hub with the passageway in flow communication with the duct in the proximal end portion of the cannula; and an extraction wire having proximal and distal ends, said wire being of smaller diameter than the longitudinal piercing member, having said distal end thereof attached to extend longitudinally from the proximal end of the longitudinal piercing member, said extraction wire extending through the duct of the cannula and through the passageway of the hub to said proximal end of said wire, an improvement comprising:
- a rigid longitudinal piercing member receiving tube having proximal and distal end portions and a longitudinal bore therethrough from said proximal to said distal end portion, said tube being adjacent to said proximal end of said hub, said extractor wire extending from said passageway through and beyond said bore of said tube;
- a first closure across said proximal end portion of said tube, said first closure having a generally central opening large enough to allow said wire to pass longitudinally therethrough but too small to allow said longitudinal piercing member to pass fully longitudinally therethrough; and
- a second closure across said distal end portion of said tube, said second closure having a generally central access through which said wire and said longitudinal piercing member can longitudinally pass;
- wherein said second closure includes means for automatically entrapping said insertion tip of said longitudinal piercing member in said longitudinal bore of said receiving tube, said entrapping means operating in response to said longitudinal piercing member being moved fully proximally into said receiving tube by proximal movement of said extraction wire; and
- said second closure comprising a disc shaped wall which is generally conically shaped and tapers rearwardly toward said proximal end portion of said tube, said access being at the apex of said conically shaped wall and adapted to frictionally engage said piercing member, whereby the wall tends to deflect the point of the piercing member away from the opening upon an attempt to extend the piercing member through the opening in a direction from the proximal end portion toward the distal end portion of the tube.

3. A sheath for removal and disposal of removable needles having attached wires and used to insert catheters, comprising:
- a rigid body having a length greater than the length of the needle and having a first opening in a first end through which said needle can extend, a second opening in a second end through which said wire attached to said needle can freely pass but through which the needle cannot pass;
- one way entrance means inside said body between the ends thereof and having a passage means beyond which said needle completely extends for insertion of the needle into a patient, said passage means engaging said needle upon retraction of the needle into said housing so as to permit the needle to be pulled by said wire through said first opening into said body and through said passage means but preventing the needle from moving in the opposite direction through said passage means, thereby retaining said needle completely encased within the body after retraction of the needle; and
- said body having a curved needle encasing portion into which the needle may be withdrawn, said curved encasing portion engaging the needle to deflect the sharpened end thereof out of alignment with the passage means, thereby preventing the needle from moving out of the body once retracted therein.

4. A sheath as claimed in claim 3, wherein:
the needle encasing portion comprises an insert in said body, said insert having a curved passage extending therethrough, whereby when the needle is withdrawn into said needle encasing portion, it is engaged along its length to deflect the sharpened point thereof out of alignment with said passage means.

5. A sheath as claimed in claim 3, wherein:
the needle encasing portion comprises an insert in said body, said insert having a curved passage extending therethrough, whereby when the needle is withdrawn into said needle encasing portion, it is engaged along its length to deflect the sharpened point thereof out of alignment with said passage means; and wherein
said one way entrance means includes a disc-shaped wall inside said body, said wall having a reduced diameter opening therethrough frictionally engaging said needle so as to enable the needle to be retracted through said opening upon pulling the wire attached to the needle, but preventing reverse movement of the needle through the opening; and
said needle encasing insert is positioned in said body between said wall and the second end of the body.

6. A sheath as claimed in claim 3, wherein:
said body is curved over at least a portion thereof, said curved body engaging the needle when the needle is withdrawn into the body to cause misalignment of the sharpened end of the needle and the passage means.

7. A sheath as claimed in claim 3, wherein:
said body is curved over at least a portion thereof, said curved body engaging the needle when the needle is withdrawn into the body to cause misalignment of the sharpened end of the needle and the passage means; and wherein
said one way entrance means includes a disc-shaped wall inside said body, said wall having a reduced diameter opening therethrough frictionally engaging said needle so as to enable the needle to be retracted through said opening upon pulling the wire attached to the needle, but preventing reverse movement of the needle through the opening; and
said curved portion of said body extends between said wall and the second end of the body.

* * * * *